(12) United States Patent
Chang

(10) Patent No.: US 8,068,169 B2
(45) Date of Patent: Nov. 29, 2011

(54) CLIP-ON VIDEO CAMERA SYSTEM FOR MEDICAL, SURGICAL AND DENTAL APPLICATIONS

(75) Inventor: Byung Jin Chang, Ann Arbor, MI (US)

(73) Assignee: General Scientific Corporation, Ann Arbor, MI (US)

( * ) Notice: Subject to any disclaimer, the term of this patent is extended or adjusted under 35 U.S.C. 154(b) by 547 days.

(21) Appl. No.: 11/741,148

(22) Filed: Apr. 27, 2007

(65) Prior Publication Data
US 2008/0204589 A1 Aug. 28, 2008

Related U.S. Application Data

(63) Continuation-in-part of application No. 11/678,637, filed on Feb. 26, 2007, now abandoned.

(51) Int. Cl.
*H04N 5/225* (2006.01)
*G03B 17/00* (2006.01)

(52) U.S. Cl. ............... 348/375; 348/373; 396/428

(58) Field of Classification Search ........... 348/373, 348/375
See application file for complete search history.

(56) References Cited

U.S. PATENT DOCUMENTS

| | | | | |
|---|---|---|---|---|
| 4,797,736 A * | 1/1989 | Kloots et al. | ........... | 348/370 |
| 5,667,291 A * | 9/1997 | Caplan et al. | ........... | 362/105 |
| 5,870,166 A | 2/1999 | Chang et al. | | |
| 6,012,827 A * | 1/2000 | Caplan et al. | ........... | 362/396 |
| 6,039,461 A * | 3/2000 | Cummings et al. | ........... | 362/287 |
| 6,120,161 A * | 9/2000 | Van Der Bel | ........... | 362/105 |
| 6,290,568 B1 | 9/2001 | Hou et al. | | |
| 6,493,136 B2 | 12/2002 | Chang et al. | | |
| 6,764,194 B1 * | 7/2004 | Cooper | ........... | 362/105 |
| 7,006,861 B2 * | 2/2006 | Flock et al. | ........... | 600/473 |
| 7,168,821 B2 * | 1/2007 | Huang | ........... | 362/103 |
| 7,253,949 B2 * | 8/2007 | Piontkowski | ........... | 359/380 |
| 7,465,078 B2 * | 12/2008 | Chang | ........... | 362/373 |
| 7,645,050 B2 * | 1/2010 | Wilt et al. | ........... | 362/103 |
| 2006/0285315 A1 * | 12/2006 | Tufenkjian | ........... | 362/105 |

FOREIGN PATENT DOCUMENTS

JP 2006006896 1/2006

* cited by examiner

Primary Examiner — Ngoc-Yen Vu
(74) Attorney, Agent, or Firm — Gifford, Krass, Sprinkle, Anderson & Citkowski, P.C.

(57) ABSTRACT

A video camera system includes a mount with a clip-on structure adapted for attachment to a pair of eyeglass frames, loupes, or a headband. The preferred embodiment includes a camera mounted on a first pivot arm, and a light source mounted on a second pivot arm. One or both of the pivot arms are rotatable, enabling the beam from the light source and field of view of the camera to be aligned for a given working distance. Polarizing filters may be mounted to the camera, light source, or both to control glare, reflection or other undesired visual artifacts.

13 Claims, 5 Drawing Sheets

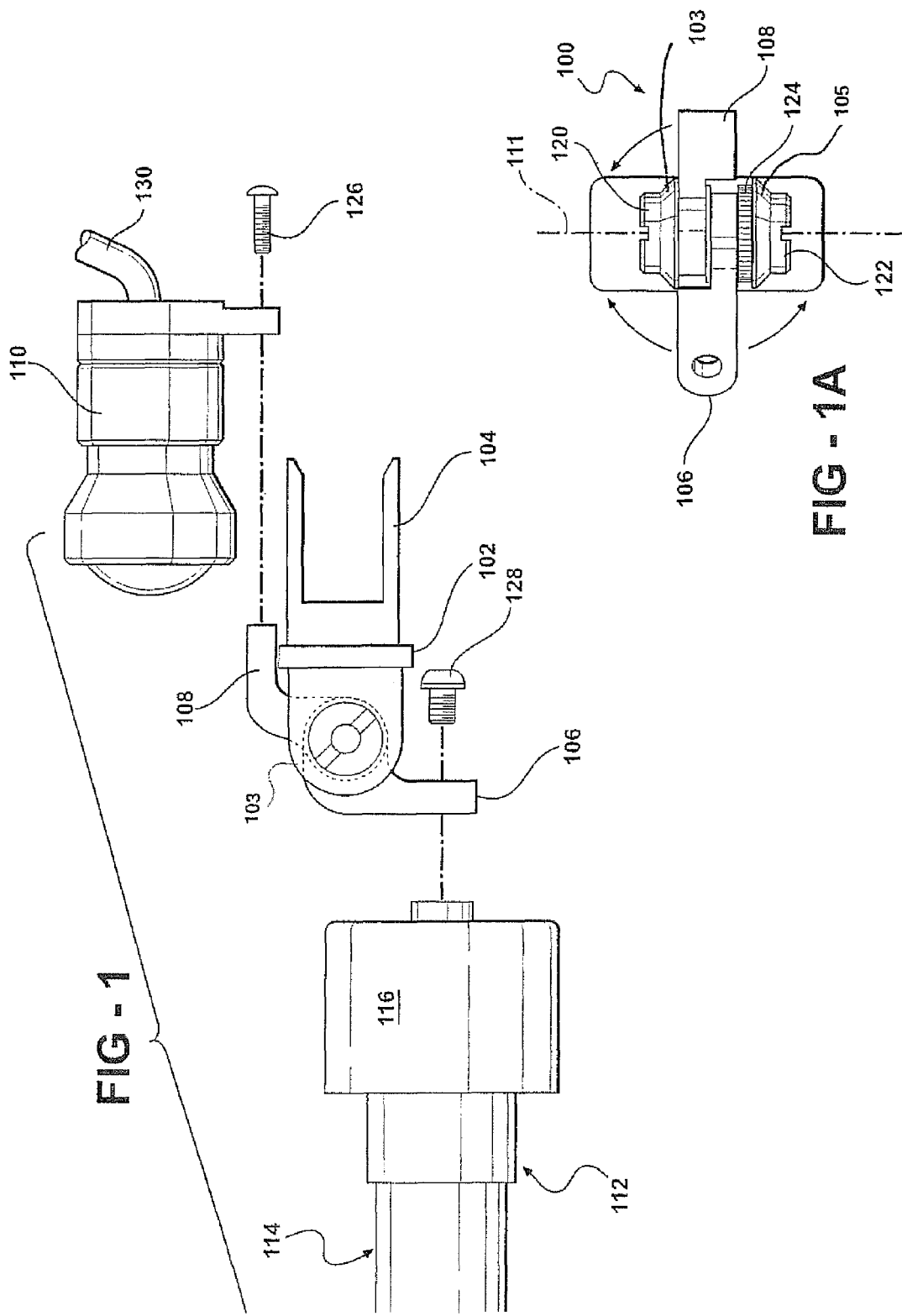

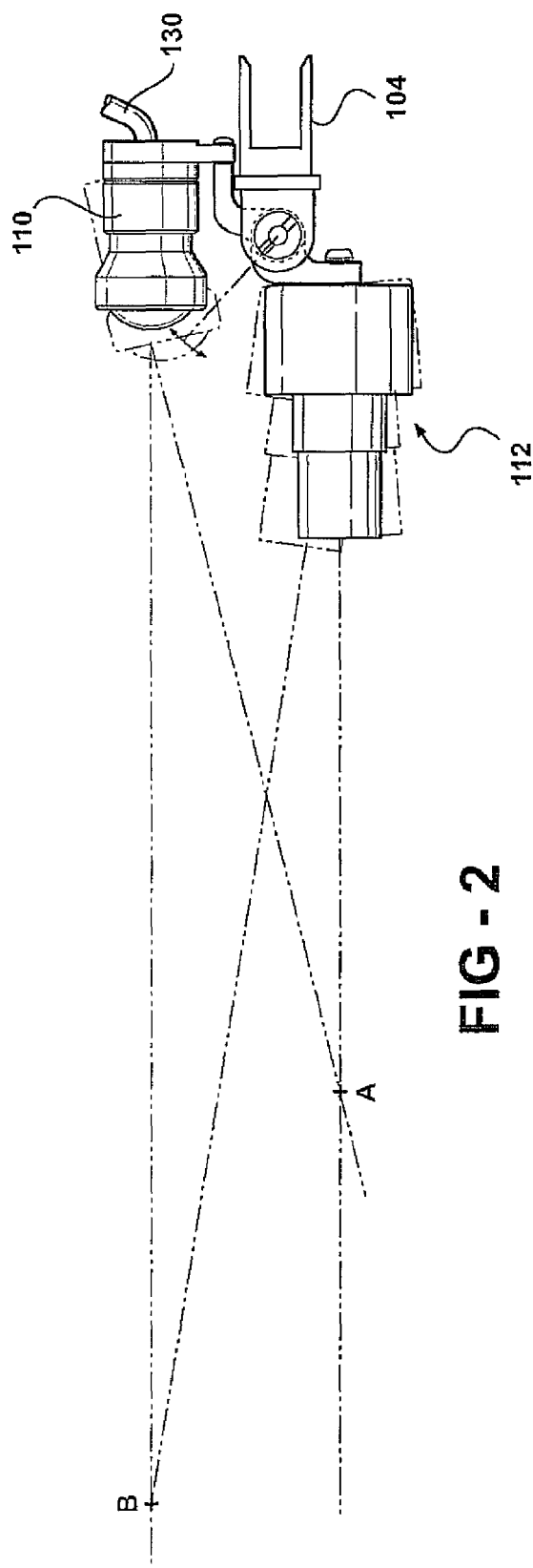

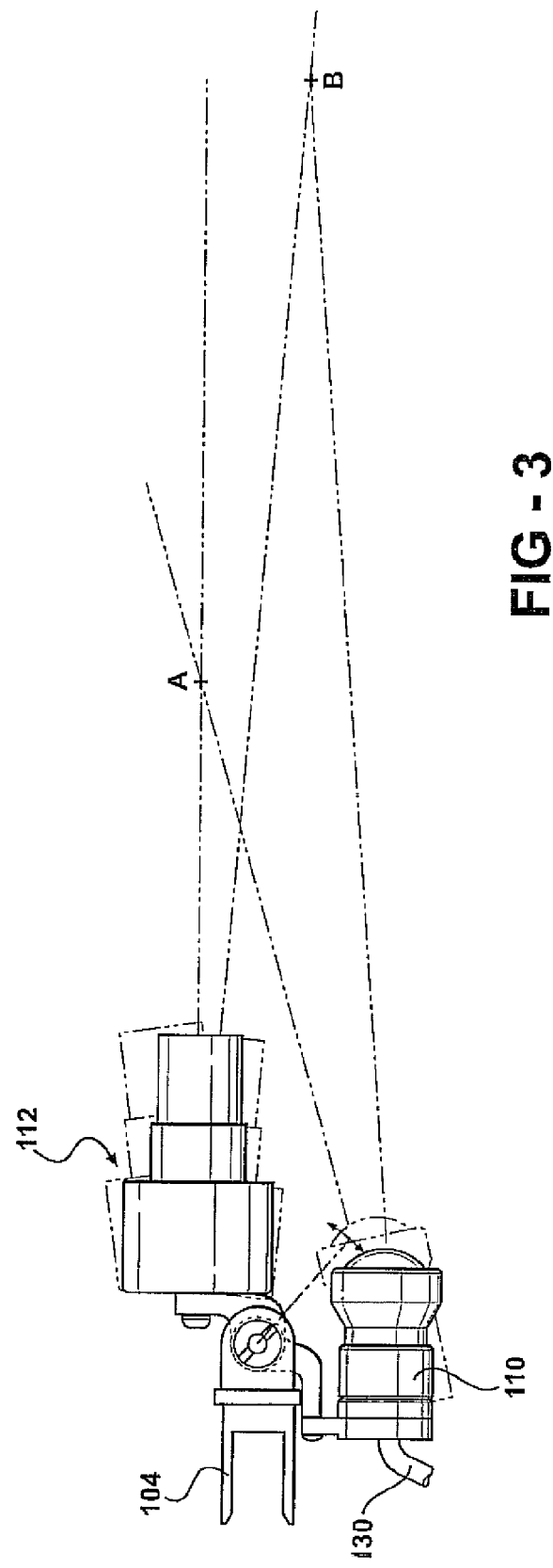

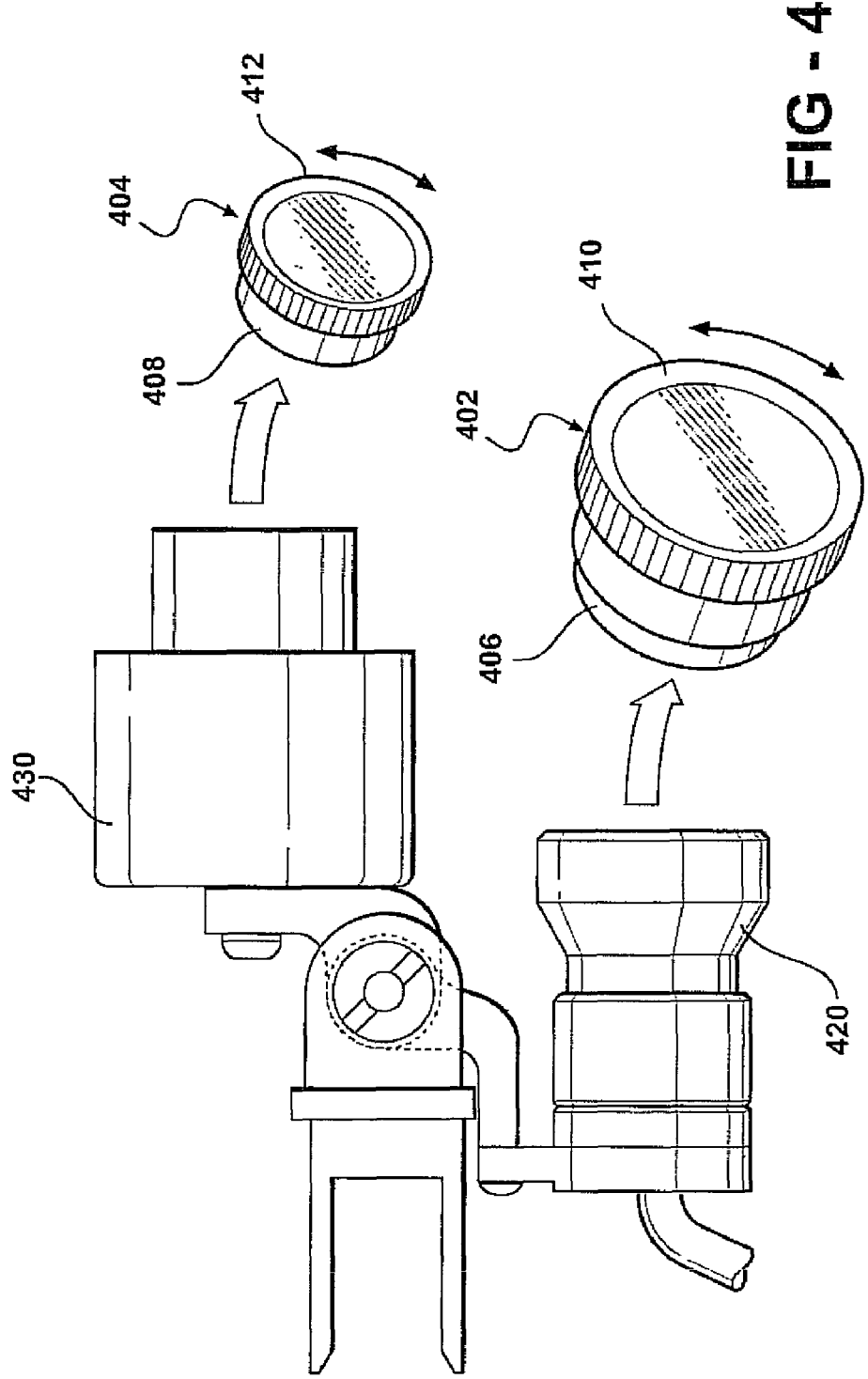

CLIP-ON VIDEO CAMERA SYSTEM FOR MEDICAL, SURGICAL AND DENTAL APPLICATIONS

REFERENCE TO RELATED APPLICATION

This application is a continuation-in-part of U.S. patent application Ser. No. 11/678,637, filed Feb. 26, 2007, the entire content of which is incorporated herein by reference.

FIELD OF THE INVENTION

This invention relates generally to head-mounted optical devices of the kind used in medical, dental and surgical procedures and, more particularly, to a clip-on camera system that may be used with an aligned light source and mounted to eyeglass frames, loupes, or a headband.

BACKGROUND OF THE INVENTION

Clip-on optical accessories are known in the art. As one example, commonly assigned U.S. Pat. No. 6,493,136 discloses an optical accessory of the type used by medical professionals with a clip-on mount, enabling the entire assembly to be used with ordinary eyeglass frames. In an alternative embodiment, the assembly may be used with specialized frames, in which case the clip-on mount may be removed for a more permanent mounting of the assembly directly to the bridge area of the eyeglass frames. In different implementations, optical accessories in the form of ocular loupes, head lamps, and miniaturized video cameras may be accommodated.

Combination camera and loupe arrangements have also been disclosed. Commonly assigned U.S. Pat. No. 5,870,166 is directed to an optical accessory mounting system that takes the form of a shaped wire frame having a proximal section attachable to the bridge portion of a pair of eyeglass frames or to a headband, a mid-section extending downwardly along and in spaced-apart conformity with the ridge of a wearer's nose, and a distal section which is preferably bent upwardly with respect to the mid-section, optionally, the mid-section may include an adjustable nose pad adapted to make contact against the ridge of the user's nose for improved weight distribution, with the distal section being configured to mountably receive one of a variety of accessories, including vision aids such as light sources, imaging apparatus such as lightweight camera devices. Although light sources and camera devices may be accommodated, and although they are independently adjustable, the wire frame configuration is bulky and somewhat awkward when used with loupe mountings.

SUMMARY OF TEE INVENTION

This invention relates generally to head-mounted optical devices of the kind used in medical, dental and surgical procedures and, more particularly, to a clip-on camera system that may be used with an aligned light source and mounted to eyeglass frames, loupes, or a headband. The preferred embodiment includes a mount with a C-shaped clip configured for attachment to a pair of eyeglass frames, loupes, or a headband.

The preferred embodiment further includes a first pivot arm coupled to the mount to which a video camera may be attached. The pivoting allows the camera to be rotated up and down relative to the mount to accommodate different fields of view. The video camera is a preferably a digital camera outputting video through a standard interface such as USB-2, FireWire, etc., for 'plug-and-play' operation.

The preferred embodiment further includes a second pivot arm coupled to the mount to which a light source is mounted. One or both of the pivot arms are rotatable, enabling the beam from the light source and field of view of the camera to be aligned for a given working distance. Polarizing filters may be mounted to the camera, light source, or both to control glare, reflection or other undesired visual artifacts

BRIEF DESCRIPTION OF THE DRAWINGS

FIGS. 1 and 1A are drawings which illustrate the preferred embodiment of the invention in unassembled form;

FIG. 2 is a drawing which shows the preferred embodiment of the invention in assembled form with different angles used to illustrate near-colinear alignment;

FIG. 3 is drawing that shows how, in the preferred embodiment, the clip-on structure is symmetrical to allow a light to be place below a camera as opposed to configuration of FIG. 2; and FIG. 4 is a drawing that shows how polarizing filters may be mounted to a light, camera, or both to reduce glare, reflection or other undesired visual artifacts.

DETAILED DESCRIPTION OF THE INVENTION

Figure 5A:
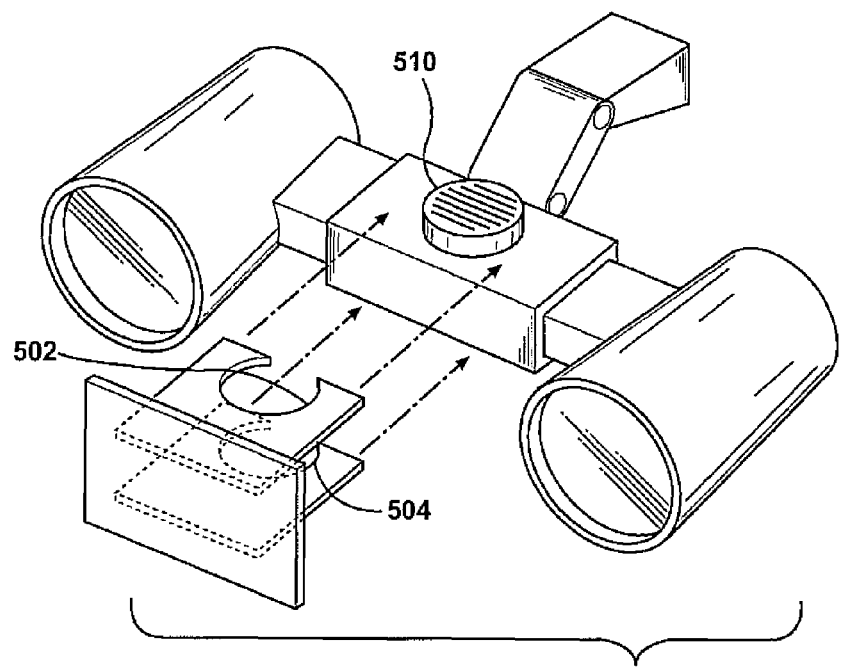
FIG. 5A is a drawing that shows one type of clip according to the invention suitable for attachment to the body of a loupe housing.

The preferred embodiment of the invention is depicted in FIGS. 1 and 1A. The system includes a mount 102 coupled to a clip structure 104 that may be used to clip onto loupes, headbands or frames. The mount 102 includes pair of opposing parallel plates 103, 105 that capture one or two pivot arms 106, 108. Although two pivot arms are shown, one for a camera (106) and another for a light source (108), the light source arm may be eliminated in place of a single arm providing a pivoting mount for the camera without a light.

If provided, the light source 110 is attached to pivot arm 108 using fastener 126, while the video camera, shown generally at 112, is attached with fastener 128. The light source includes a cable 130 bring electricity to an LED or incandescent bulb within housing 110, or the cable 130 may be an optical fiber bring light from a remote source. The video camera 112 includes an electronic unit 116 and imaging lens 114 with optional zoom. The cable from the camera unit 112 to a computer interface is not shown in the drawings. The preferred camera generates video files in an electronic format, as well as digital pictures in "jpeg" or other formats. This allows digital images to be stored directly to a hard drive of a personal computer or any other digital monitor system for real-time viewing. The clip-on mounting structure is fully compatible with analog cameras as well.

One or both of the camera and light source are pivotable, enabling the beam from the light source and field of view of the camera to be aligned for a given working distance. In the preferred embodiment, both pivot arms 106, 108 pivot, and to save on hardware, they do so about a common axis 111, with separate adjustable fasteners 120, 127 being used for stabilization of the two pivot arms. An optional washer 124 is used to control friction.

As shown in FIG. 2, by virtue of the independent rotation of the light source 110 and camera 11, near-collinear operation may be established at different points such as A and B shown in the drawing, such that at a particular working distance, the field of view of the camera and the illumination of the light are very well aligned.

In the preferred embodiment, the clip structure is symmetrical, allowing the assembly to be tuned around with the camera placed above the light, as shown in FIG. 3. As shown in FIG. 4, polarizing filters 402, 404 may be mounted to light 420, camera 430, or both, to reduce glare or other undesired visual artifacts. Each polarizer preferably includes a rear, threaded ring 406, 408 for mounting on the light or camera, and a forward ring 410, 412 that may be rotated once mounted to adjust the level of glare or reflection control.

Figure 5B:
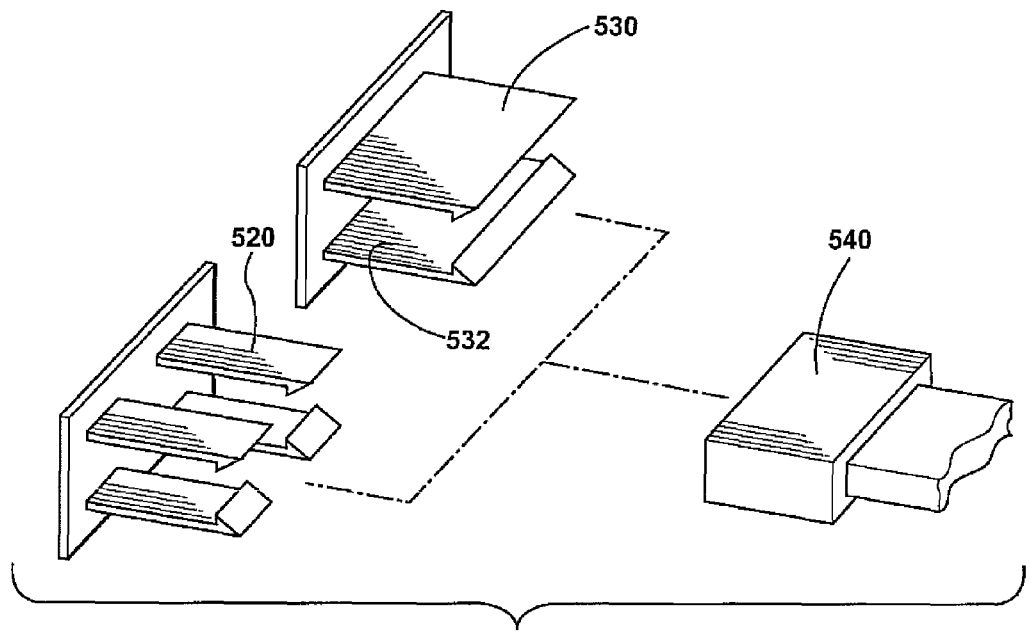
FIG. 5B is a drawing that shows a different clip according to the invention including a plurality of prongs and a structural feature to which this or other clip styles attaches.

Different clip structures are possible according to the invention. FIG. 5A is a drawing that shows one type of clip according to the invention suitable for attachment to the body of a loupe housing. This clip includes circular or oval cut-outs that engages with an interpupillary control knob 510 found on loupe housings. FIG. 5B is a drawing that shows a different clip according to the invention including a plurality of prongs 520. FIG. 5B also shows a further clip according to the invention having a pair of opposing prongs 530, 532. In all embodiments shown the clip is symmetrical such that it may be removed, rotated 180 degrees and re-applied, though this is not necessary according to the invention. If a structure such as a loupe housing is not available, a mounting block such as 540 may be attached to eyeglass frames or a headband to receive the clip.

I claim:

1. An optical mounting system, comprising:
   a mount including a clip-on structure for coupling to a pair of eyeglass frames, loupes, or a headband;
   the clip-on structure including a pair of parallel, spaced-apart upper and lower plates;
   a first pivot arm coupled to the mount;
   a video camera mounted on the first pivot arm,
   whereby, when the mount is clipped to a pair of eyeglass frames, loupes, or headband, the camera may be pivoted in a vertical plane to accommodate a desired field of view.

2. The optical mounting system of claim 1, further comprising:
   a second pivot arm coupled to the mount;
   a light source outputting a beam of light mounted on the second pivot arm; and
   wherein both the first and second pivot arms are rotatable in the same plane, enabling the beam from the light source and field of view of the camera to be aligned for a given working distance.

3. The optical mounting system of claim 2, wherein the clip structure allows the camera to be positioned above the light source or vice versa.

4. The optical mounting system of claim 2, wherein each of the parallel, spaced-apart upper and lower plates includes a generally circular cut-out.

5. The optical mounting system of claim 2, wherein each of the parallel, spaced-apart upper and lower plates includes a barb structure facing the opposing plate.

6. The optical mounting system of claim 2, wherein the first pivot arm and the second pivot arm sharing a common axis of rotation.

7. The optical mounting system of claim 1, further including a polarizing filter mountable on the light source.

8. The optical mounting system of claim 1, wherein the camera is a digital camera.

9. The optical mounting system of claim 1, further including a polarizing filter mountable on the camera.

10. An optical mounting system, comprising:
    a mount including a clip-on structure for coupling to a pair of eyeglass frames, loupes, or a headband;
    a first pivot arm coupled to the mount;
    a video camera mounted on the first pivot arm;
    a second pivot arm coupled to the mount, the first pivot arm and the second pivot arm sharing a common axis of rotation;
    a light source outputting a beam of light mounted on the second pivot arm; and
    whereby, when the mount is clipped to a pair of eyeglass frames, loupes, or headband, the camera and light source may be pivoted in the same plane, enabling the beam from the light source and field of view of the camera to be aligned for a given working distance.

11. The optical mounting system of claim 10, wherein the clip structure allows the camera to be positioned above the light source or vice versa.

12. The optical mounting system of claim 10, further including a polarizing filter mountable on the camera.

13. The optical mounting system of claim 10, further including a polarizing filter mountable on the light source.

* * * * *